United States Patent [19]

Kuroiwa et al.

[11] Patent Number: 5,151,372
[45] Date of Patent: Sep. 29, 1992

[54] METHOD FOR DETERMINATION OF HYDROXYACETOPHENONE DERIVATIVES

[75] Inventors: Katsumasa Kuroiwa; Katsuhiro Katayama; Toshihide Miura, all of Koriyama; Takeshi Nagasawa, Urawa, all of Japan

[73] Assignee: Nitto Boseki Co., Ltd., Fukushima, Japan

[21] Appl. No.: 483,903

[22] Filed: Feb. 22, 1990

[30] Foreign Application Priority Data

Mar. 8, 1989 [JP] Japan .................................. 1-055696

[51] Int. Cl.$^5$ ..................... G01N 21/00; G01N 31/00; G01N 33/00
[52] U.S. Cl. ......................................... 436/164; 436/8; 436/88; 436/128; 436/131; 436/171
[58] Field of Search ..................... 436/88, 8, 131, 128, 436/171, 164

[56] References Cited

U.S. PATENT DOCUMENTS 5,081,274  1/1992  Kuroiwa et al. ................... 358/198

OTHER PUBLICATIONS

Chem. Abst. 114:159857d, 1991.
Chem. Abst. 94:184914w, 1981.
Chem. Abst. 92:140047v, 1980.

*Primary Examiner*—John W. Rollins
*Attorney, Agent, or Firm*—Darby & Darby

[57] ABSTRACT

There is provided a method for determination of hydroxyacetophenone derivatives such as 3,5-dichloro-4-hydroxyacetophenone in the presence of protein such as albumins or globulins with high sensitivity. The hydroxyacetophenone derivative can be measured in the neutral to acidic region, whereby the method is not affected by interferrants such as bilirubin or hemoglobin. The hydroxyacetophenone derivatives are useful as the chromogen of synthetic substrates for determining acid phosphatase activity.

6 Claims, 3 Drawing Sheets

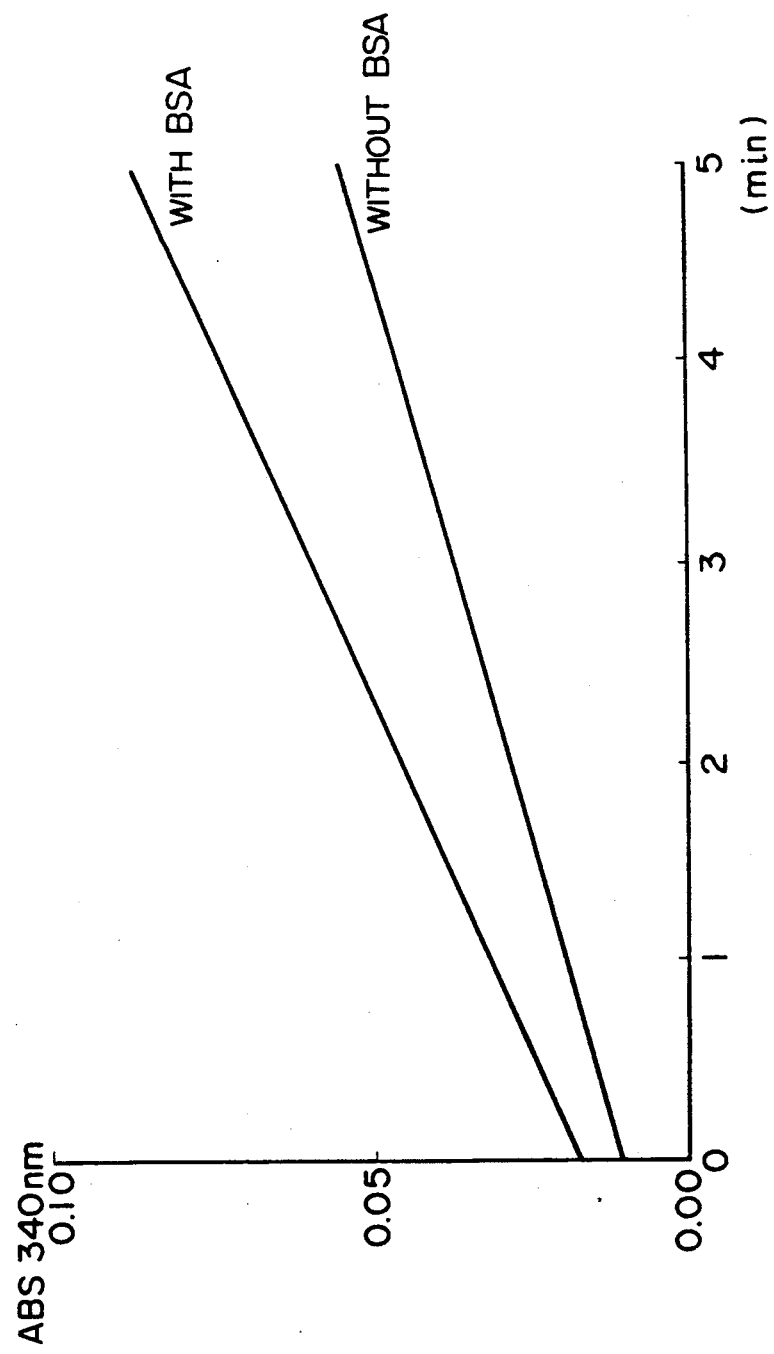

METHOD FOR DETERMINATION OF HYDROXYACETOPHENONE DERIVATIVES

BACKGROUND OF THE INVENTION

1. Field of the Invention

The present invention relates to a method for determination of hydroxyacetophenone derivatives. More particularly, the present invention relates to a method for determination of hydroxyacetophenone derivatives which comprises measuring hydroxyacetophenone derivatives represented by general formula (I):

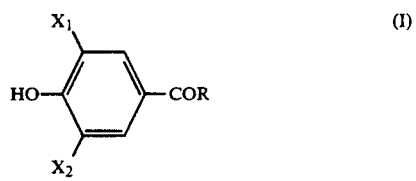

wherein R represents —$(CH_2)_nCH_3$ (n=0 to 3); and $X_1$ and $X_2$ independently represents a halogen atom or hydrogen atom, in association with protein. The present invention also relates to a method for determination of a hydrolase activity utilizing such a measurement method. Hydroxyacetophenone derivatives are useful as the chromogen of synthetic substrates for determining a hydrolase activity. Therefore, by applying the methods described above, the activity of hydrolases such as acid phosphatase or the like can be determined with high sensitivity.

2. Prior Art Statement

In general, hydroxyacetophenone derivatives can be determined by measuring their absorbance 340 nm with a spectrophotometer since the maximum absorption of their absorption spectra exists at about 340 nm. Hydroxyacetophenone derivatives have a structure containing a hydroxy group therein. By utilizing the hydroxy moiety for ester bond or ether bond, the derivatives are expected to be promising as the chromogen of synthetic substrates for determining the hydrolase activity, which are used for clinical inspections.

In recent clinical inspections, the main trend is by means of an automated analyzer. For this reason, synthetic substrates available to analysis of an initial velocity are desired also in activity measurement of enzyme adoptable to automated analysis. With respect to hydrolases such as acid phosphatase, N-acetylglucosaminidase, β-galactosidase, α-amylase, etc. which have the optimum pH in the range of neutral to acidic regions, however, there are known few chromogens that can be colorimetrically determined in the rang of neutral to acidic regions so that the initial velocity method has not spread very widely. Methods for determination of the activity of these enzymes using conventional synthetic substrates are roughly classified into the following 3 types, in which chromogens used are also illustratively given.

(a) Method which comprises using p-nitrohenylphosphoric acid as substrate, adding an alkali to the chromogenic p-nitrophenol hydrolyzed and released upon enzyme reaction and colorimetrically determining the chromogen quantitatively [Hudson, P. B.: J. Urol., 58, 89 (1947)]

(b) Method which comprises using phenylphosphoric acid as substrate, condensing the similarly released chromogenic phenol with other compounds and colorimetrically determining the chromogen quantitatively [Kind, P. R. N., King, E. J.: J. Clin. Path., 7, 322 (1954)]

(c) Method which comprises using 2,6-dichloro-4-nitrophenylphosphoric acid as substrate and quantitatively determining the chromogenic 2,6-dichloro-4-nitrophenol colorimetrically as it is [Teshima, S., Hayashi, Y., Ando, M.: Clin. Chim. Acta, 168, 231 (1987)]

However, in the methods (a) and (b) described above, a color-forming reaction for termination and condensation are required, respectively so that it is impossible to conduct a rate assay. In the method (c), it is possible to perform the initial velocity analysis. However, substrates obtained using currently found chromogens involve problems that they tend to cause spontaneous hydrolysis and are unstable and furthermore, 2,6-dichloro-4-nitrophenol as the chromogen is measured at about 400 nm and the substrates are thus liable to be affected by the coexisting substances such as bilirubin or hemoglobin in body fluids such as serum or urine.

In this regard, the hydroxyacetophenone derivatives can be expected to as the chromogen of substrates for determination of hydrolases described above, since their wavelength for measurement can be set at about 340 nm which is affected only with difficulty by the coexisting substances.

However, use of the hydroxyacetophenone derivatives alone does not result in sufficiently large absorption at 340 nm. In addition, dissociation of the hydroxy group is also insufficient in the acidic region. Thus, the hydroxyacetophenone derivatives encounter problems that their sensitivity for measurement is poor and the initial velocity method does not satisfactorily work in the acidic region. Such problems remain unsolved yet.

In order to solve the foregoing problems, the present inventors have made extensive investigations and have reached the present invention. That is, the present inventors have made investigations of the use hydroxyacetophenone derivatives represented by general formula (I) described below, in association with protein, in the UV measurement method at about 340 nm. As a result, they have found that there is an increase in the absorption peak at about 340 nm, i.e., an increase in molecular extinction coefficient ε and acceleration of dissociation of the hydroxy group at the acidic region, i.e., a shift of pKa showing a pH value in 50% dissociation of the hydroxy group in the hydroxyacetophenone derivatives toward the acidic region. They have also found that in this case, the measurement sensitivity can be increased, it becomes possible to perform the measurement at the acidic region, and even in the case of using as the chromogen of substrates for determination of hydrolase activity, the measurement sensitivity can be increased, it becomes possible to perform the initial velocity method at the acidic region.

SUMMARY OF THE INVENTION

That is, the present invention relates to a method for determination of hydroxyacetophenone derivatives which comprises measuring hydroxyacetophenone derivatives represented by general formula (I):

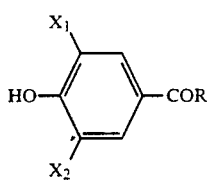

wherein R represents $-(CH_2)_nCH_3$ (n=0 to 3); and $X_1$ and $X_2$ independently represents a halogen atom or hydrogen atom], in association with protein. The present invention also relates to a method for determination of a hydrolase activity utilizing such a measurement method. It is thus an object of the present invention to provide a method for determination of the hydroxyacetophenone derivatives which enables to measurement in the acidic region with high sensitivity.

Another object of the present invention is to provide a method for determination of the hydroxyacetophenone derivatives without being affected by bilirubin, hemoglobin, etc. in body fluids.

A further object of the present invention is to provide a method for determination of the hydroxyacetophenone derivatives which is applicable to the initial velocity method.

These and other objects and advantages will be apparent from the following description.

BRIEF DESCRIPTION OF THE DRAWINGS

FIG. 3 indicates a reaction time course of 2,6-dichloro-4-acetylphenylphosphoric acid.

DETAILED DESCRIPTION OF THE INVENTION

In the formula (I) described above, examples of R include methyl, ethyl, propyl and butyl. $X_1$ and $X_2$ independently represents a halogen exemplified by fluorine, chlorine, bromine, etc.

The compounds represented by general formula (I) can be readily obtained, for example, by Fries rearrangement of the corresponding phenol ester compounds (Japanese Patent Application No. 63-234555).

The protein which can be used in association with the compounds of formula (I) may be any protein so long as it is water soluble. Examples of such protein include albumins such as human serum albumin, bovine serum albumin, etc.; globulins such as γ-globulin, etc. A concentration of these proteins is not particularly limited but it may be sufficient that the protein is contained preferably in a concentration of approximately 0.1 to 1% in a buffer solution used in performing the method of the present invention.

The term "in association with protein" as used herein refers to the system in which protein is allowed to coexist in the measurement system. More specifically, the protein may be mixed with the hydroxyacetophenone derivatives of formula (I); may be dissolved in a buffer solution used in the measurement system and the solution is mixed with the compounds of formula (I). In any event, it is sufficient to attain the effects of the present invention whatsoever the protein is present in the measurement system, in combination with the hydroxyacetophenone derivatives of formula (I).

As the buffer solution, any conventional buffer solution is usable as long as the solution has a buffering ability in the range of from the neutral to acidic regions. Examples of the buffer solution include buffer solutions of citric acid, acetic acid, succinic acid, phthalic acid, phosphoric acid, boric acid, etc. If necessary and desired, a surface active agent, a preservative, a stabilizer and the like may also be added to these buffer solutions.

Changes in $\epsilon$ at 340 nm ($\epsilon_{340}$) and pKa of the hydroxyaetophenone derivatives in the presence of or absence of protein were examined The results are shown below.

EXPERIMENT 1

A buffer solution containing 0.0286M citric acid, $KH_2PO_4$, boric acid, diethylbarbituric acid and 0.1% Triton X-100, and a buffer solution further supplemented with 0.3% bovine serum albumin (hereafter simply referred to as BSA, manufactured by Sigma, Inc.) were adjusted to pH ranges of from 3 to 10. To 0.38 ml of each of these buffer solutions, was added 0.02 ml of each of the hydroxyacetophenone derivatives shown in Table 1 below, which had been adjusted to 0.1 mM. Using a spectrophotometer, absorbance of each solution was measured at 340 nm.

Figure 1:
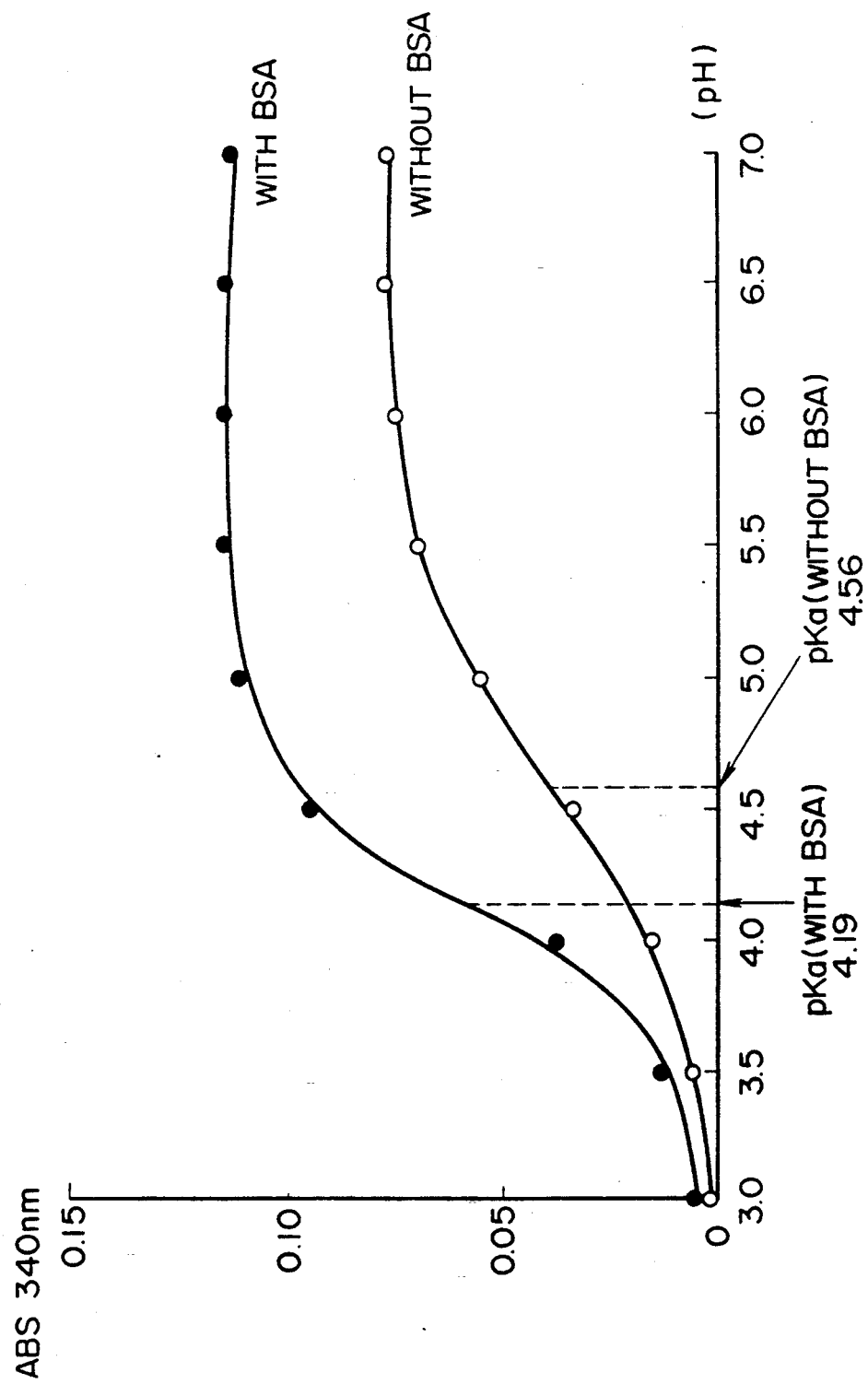
FIG. 1 shows a dissociation curve of 3,5-dichloro-4-hydroxyacetophenone.

In this case, $\epsilon_{340}$ and pKa of each of the hydroxyacetophenone derivatives in the presence or absence of BSA are shown in Table 1. In addition, changes in absorbance of 3,5-dichloro-4-hydroxyacetophenone at various pH values and its pKa are shown in FIG. 1 (absorbance of the buffer solution itself is removed from the absorbance shown).

TABLE 1

| | | | $\epsilon_{340}$ (l · mol$^{-1}$ · cm$^{-1}$) × 10$^{-3}$ (pH 6.0) BSA, 0.3% | | pKa BSA, 0.3% | |
|---|---|---|---|---|---|---|
| R | $X_1$ | $X_2$ | None | Added | None | Added |
| $CH_3$ | F | F | 12.7 | 14.3 | 5.13 | 4.94 |
| $CH_3$ | Cl | Cl | 14.9 | 22.9 | 4.56 | 4.19 |
| $CH_3$ | Br | Br | 16.7 | 24.2 | 4.50 | 4.02 |
| $CH_3$ | Cl | H | 4.9 | 6.9 | 6.43 | 6.03 |
| $CH_3$ | Br | H | 5.3 | 9.7 | 6.37 | 5.81 |
| $C_3H_7$ | Cl | Cl | 15.0 | 16.7 | 4.89 | 4.00 |

As is clear from these results, the hydroxyacetophenone derivatives can increase $\epsilon_{340}$ by about 10% to about 80% in the presence of BSA. In addition, pKa is also shifed to the acidic region by approximately 0.2 to 0.9. Therefore, according to the method of the present invention, it is possible to determine the hydroxyacetophenone derivatives in the acidic region with higher sensitivity than in conventional methods.

According to the present invention, the determination of the hydroxyacetophenone derivatives represented by general formula (I) can be generally carried out as follows. That is, after a solution of the hydroxyacetophenone derivative to be determined is mixed with a buffer solution containing a suitable protein, its absorbance is measured at 300 to 370 nm, preferably at the maximum wavelength of from 330 to 340 nm, using a spectrophotometer. An amount of the hydroxyacetophenone derivative to be measured is determined by comparing the standard curve preliminarily obtained by similarly performing with respect to known amounts of the hydroxyacetophenone derivative.

The measurement method of the present invention is applicable to determination of the activity of hydrolases having the optimum pH in the range of neutral to acidic regions, such as acidic phosphatase, N-acetylglucosamidase, β-galactosidase, α-amylase, etc., using, e.g., the initial velocity method. That is, when synthetic substrates for determining such enzymes using the hydroxyacetophenone derivative as the chromogen and the enzyme to be determined are subjected to enzyme reaction and the protein is present in the measurement system, the hydroxy group released from the hydroxyacetophenone derivative as the chromogen upon the enzyme reaction is sufficiently dissociated even in the range of neutral to acidic regions and $\epsilon$ also increases. By measuring an increase of the absorbance per one minute, the activity of the enzyme can be determined by the initial velocity method with high sensitivity. As the synthetic substrate for determining the hydrolase activity in which the hydroxyacetophenone derivative is used as the chromogen, there are phosphoric acid derivatives such as 2,6-dichloro-4-acetylphenylphosphoric acid, etc. obtained by binding, e.g., hydroxyacetophenone derivatives with phosphoric acid through ester bond (Japanese Patent Application No. 63-234555). By using the phosphoric acid derivatives as substrate, especially acid phosphatase activity can be determined with high sensitivity.

According to the present invention, the problems encountered in conventional methods have been solved in various points. The advantages of the present invention are given below.

(1) The present invention provides the following advantages by using the hydroxyacetophenone derivative as the chromogen of synthetic substrates for determining hydrolase activity which have the optimum pH in the neutral to acidic regions and by determining the hydrolase activity in the co-presence of protein in the measurement system.

(a) Even in the acidic region, the hydroxy group of the hydroxyacetophenone derivative is sufficiently dissociated so that it becomes possible to measure the hydrolase activity by the initial velocity method. Thus, an automated analyzer is applicable to the determination of hydrolase activity.

(b) Due to increased $\epsilon$ of the hydroxyacetophenone derivative, the measurement sensitivity of the enzyme activity increases.

(c) The wavelength for measurement can be set in the UV region of from 300 to 370 nm and hence, the method is affected only with difficulty, upon measurement, by coexisting substances such as bilirubin, hemoglobin, etc. in body fluids.

(2) In the measurement of the hydroxyacetophenone derivative, the following advantages are given by allowing protein to coexist.

(a) Since pKa of the hydroxyacetophenone derivative is shifted to the acidic region, it has become possible to measure the hydroxyacetophenone derivative in an acidic solution, which was impossible before.

(b) Because of increased $\epsilon$ of the hydroxyacetophenone derivative, the measurement sensitivity increases.

As described above, the method for measurement of the present invention not only provides an improvement in determining the hydroxyacetophenone derivative but also enables to perform the initial velocity analysis for determination of the hydrolase activity having the optimum pH in the neutral to acidic regions which leads to application of the present method to an automated analyzer. Therefore, the present invention greatly contributes to the field of clinical tests.

EXAMPLES

Hereafter the present invention is described in more detail with reference to the examples below but is not deemed to be limited thereto.

EXAMPLE 1

Standard curve of the hydroxyacetophenone derivative

Figure 2:
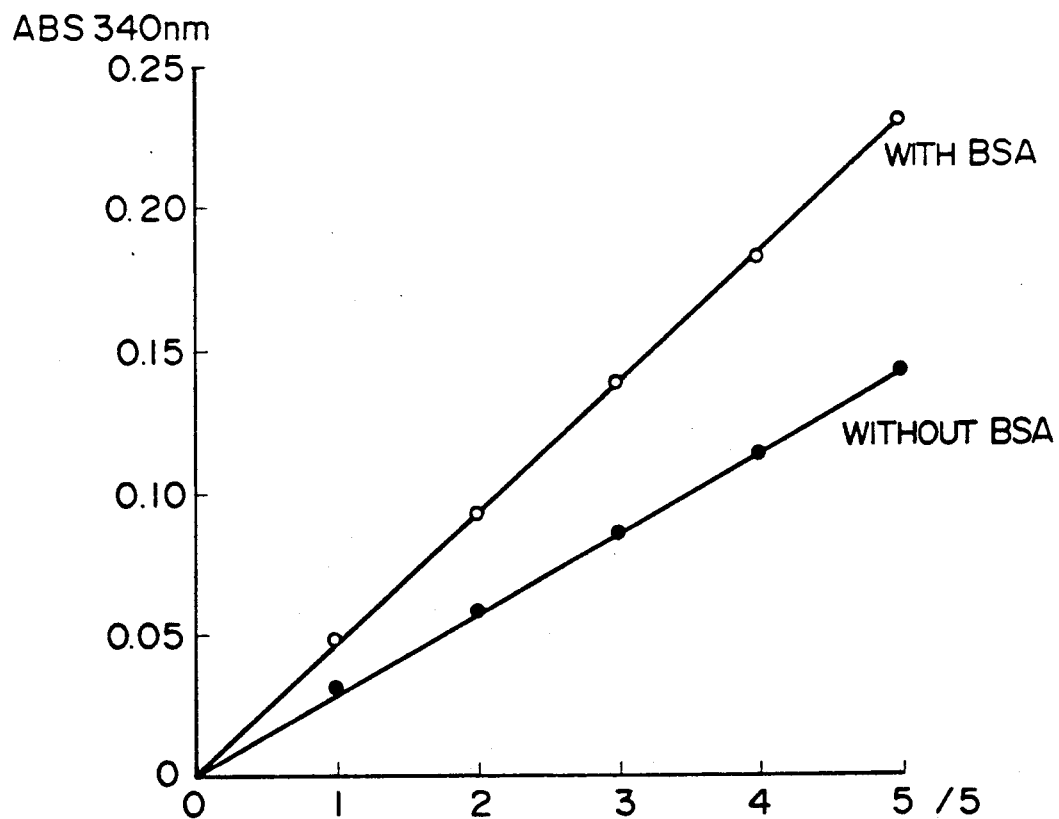
FIG. 2 is a graph showing a standard curve for 3,5-dichloro-4-hydroxy-acetophenone.

As a stock solution (5/5), 0.2 mM solution of 3,5-dichloro-4-hydroxyacetophenone was used. The solution was diluted with purified water to prepare 5-stage serial dilutions. To 0.02 ml of the solution in each concentration was mixed with 0.38 ml each of 0.1M citrate buffer solution (pH 5.4) containing 0.1% Triton X-100 and a buffer solution further supplemented with 0.3% BSA. Each absorbance was measured at 340 nm with a spectrophotometer to prepare the standard curve (FIG. 2).

As is clear from the drawing, when BSA is present, the absorbance is extremely large Therefore, as compared to the case where BSA is absent, the measurement sensitivity is greatly improved. Since the graph shows the proportional relationship up to 5/5, it is possible to quantitatively determine 3,5-dichloro-4-hydroxyacetophenone up to 0.01 mM.

EXAMPLE 2

Determination of Acid Phosphatase Using Substrate Obtained by Using the Hydroxyacetophenone Derivative as the Chromogen The activity of acid phosphatase in a vital sample solution was determined using 2,6-dichloro-4-acetylphenylphosphoric acid, which was obtained using 3,5-dichloro-4-hydroxyacetophenone as the chromogen. The substrate was synthesized according to the method described in Japanese Patent Application No. 63-234555 The outline of the measurement is described below.

In 0.01M citrate buffer solution (pH 3.0) was dissolved 2,6-dichloro-4-acetylphenylphosphoric acid to make 6 mM substrate solution A sample (prostatic acid phosphatase; manufactured by Sigma, Inc.; 0.02 ml) was added to 0.4 ml each of 0.1M citrate buffer solution (pH 5.4) containing 0.1% Triton X-100 and a buffer solution further supplemented with 0.3% BSA. After warming at 37° C. for 3 minutes, 0.1 ml of the substrate solution was added thereto to initiate the reaction A change in absorbance was measured at 340 nm and the change in absorbance per one minute was determined (for the measurement, Model No. 7050 automated analyzer manufactured by Hitachi Ltd. was used).

The change in absorbance per one minute ($\Delta E$/min) and data (blank) obtained using physiological saline as a sample solution are shown in Table 2. The time course for 5 minutes is shown in FIG. 3.

TABLE 2

| Presence or Absence of 0.3% BSA | Sample Prostatic Acid Phosphatase *($\Delta E$/min) | Physiological Saline (blank) ($\Delta E$/min) |
| --- | --- | --- |
| None | 0.0864 | 0.0012 |

TABLE 2-continued

| Presence or Absence of 0.3% BSA | Sample Prostatic Acid Phosphatase *(ΔE/min) | Physiological Saline (blank) (ΔE/min) |
|---|---|---|
| Presence | 0.1345 | 0.0029 |

*(Blank value is compensated)

As is obviously noted from the results, ΔE/min becomes about 1.6 times by the addition of BSA so that the measurement sensitivity increases. Since an increase in the blank value is small, the substrate is stable. Furthermore, since the time course for 5 minutes is in the linear relationship, the acid phosphatase activity can be determined by the initial velocity method, using the substrate in which the hydroxyacetophenone derivative of the present invention is used as the chromogen, in association with protein.

What is claimed is:

1. A method for the determination of a hydroxyacetophenone derivative which comprises measuring a UV absorbance of said derivative, in association with a protein, said derivative represented by formula (I):

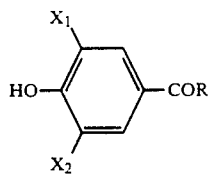

wherein R represents —$(CH_2)_nCH_3$ ($n=0$ to 3); and $X_1$ and $X_2$ independently represents a halogen atom or hydrogen atom.

2. A method according to claim 1, wherein said hydroxyacetophenone derivative is 3,5-dichloro-4-hydroxyacetophenone.

3. A method according to claim 1, wherein said protein is selected from the group consisting of albumin and globulin.

4. A method according to claim 3, wherein said albumin is selected from the group consisting of human serum albumin and bovine serum albumin.

5. A method according to claim 3, wherein said globulin is γ-globulin.

6. A method according to claim 1, wherein said absorbance is measured at a wavelength from 300 to 370 nm.

* * * * *